US008748591B2

(12) United States Patent
Weaver et al.

(10) Patent No.: US 8,748,591 B2
(45) Date of Patent: Jun. 10, 2014

(54) CHIMERIC SINDBIS-WESTERN EQUINE ENCEPHALITIS VIRUS AND USES THEREOF

(75) Inventors: Scott C. Weaver, Galveston, TX (US); Ilya Frolov, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 50 days.

(21) Appl. No.: 12/148,172

(22) Filed: Apr. 17, 2008

(65) Prior Publication Data

US 2008/0260698 A1   Oct. 23, 2008

Related U.S. Application Data

(60) Provisional application No. 60/923,987, filed on Apr. 17, 2007.

(51) Int. Cl.
*C07H 21/04* (2006.01)
*A61K 35/00* (2006.01)
*C12N 15/63* (2006.01)

(52) U.S. Cl.
USPC ............ 536/23.72; 424/93.1; 435/320.1

(58) Field of Classification Search
USPC ............ 536/23.72; 424/93.1; 435/320.1
See application file for complete search history.

(56) References Cited

U.S. PATENT DOCUMENTS

| 6,592,874 B2 * | 7/2003 | Schlesinger et al. ....... 424/218.1 |
| 2003/0119182 A1 | 6/2003 | Smith et al. |
| 2008/0260698 A1 | 10/2008 | Weaver et al. |
| 2010/0247565 A1 | 9/2010 | Frolov et al. |

OTHER PUBLICATIONS

Paessler et al, (Journal of Virology, 77(17): 9278-9286, 2003).*
Yan et al. (2000, Science 290:523-527).*
Ahola, et al., "Effects of Palmitoylation of Replicase Protein nsP1 on Alphavirus Infection", J Virol, Aug. 2000, pp. 6725-6733, vol. 74(15).
Alice, "Infeccao Humana Pelo Virus "Leste" Da Encefalite Equina", Boletim do Instituto Biologico da Bahia, 1956, pp. 3-9 vol. 3.
Anishchenko, et al., "Generation and Characterization of Closely Related Epizootic and Enzootic Infectious cDNA Clones for Studying Interferon Sensitivity and Emergence Mechanisms of *Venezuelan equine encephalitis virus*", J Virol, Jan. 2004, pp. 1-8, vol. 78(1).
Baxeyanis, Nucleic Acids Res, 2003, pp. 1-10, vol. 31.
Bernard, et al., Virology, 2000, pp. 93-103, vol. 276(1).
Brault, et al., "Positively Charged Amino Acid Substitutions in the E2 Envelope Glycoprotein Are Associated with the Emergence of *Venezuelan equine encephalitis virus*", J Virol, Feb. 2002, pp. 1718-1730, vol. 76(4).
Brault, et al, "*Venezuelan equine encephalitis* emergence: Enhance vector infection from a single amino acid substitution in the envelope glycoprotein", Proc Natl Acad Sci USA, Aug. 3, 2004, pp. 11344-11349, vol. 101(31).
Broeck et al., "A Serological Difference Between Eastern and Western Equine Encephalomyelitis Virus", Experimental Biology and Medicine, 1933, pp. 217-220, vol. 31.
Brown, et al., "Attenuation and Immunogenicity of ts Mutants of Eastern Encephalitis Virus for mice", J Gen Virol, Jan. 9, 1975, pp. 111-116, vol. 27.
Brynes & Griffin, "Binding of *Sindbis virus* to Cell Surface Heparan Sulfate", J Virol, Sep. 1998, pp. 7349-7356, vol. 72(9).
Calisher, et al., Intervirology, 1980, pp. 229-232, vol. 14(5-6).
Calisher, et al., "Arbovirus serogroups: definition and geographic distributioin", MTP, editor, translator and editor The Arboviruses: Epidemiology and Ecology, 1988, pp. 19-57, vol. 1.
Casals, "Antigenic Variants of Eastern Equine Encephalitis Virus", J Exp Med, 1964, pp. 547-565, vol. 119.
Causey, et al., Revista Servico Especial Saude Publica, 1962, pp. 47-50, vol. 12.
Causey and Theiler, "Virus Antibody Survey on Sera of Residents of the Amazon Valley in Brazil", Am J Trop Med Hyg, 1958, pp. 36-41, vol. 7(1).
Charles, et al., "Mechanism of Neuroinvasion of *Venezuelan equine encephalitis virus* in the Mouse", Virology, Jan. 13, 1995, pp. 662-671, vol. 208(2).
Davis, et al., "A single nucleotide change in the E2 glycoprotein gene of *Sindbis virus* affects penetration rate in cell culture and virulence in neonatal mice", Proc Natl Acad Sci USA, Sep. 1986, pp. 6771-6775, vol. 83(18).
Davis, et al., "Attenuating Mutations in the E2 Glycoprotein Gene of *Venezuelan equine encephalitis virus*: Construction of Single and Multiple Mutants in a Full-Length cDNA Clone", Virology, 1991, pp. 20-31, vol. 183(1).
Dremov, et al., Acta Virol, 1978, pp. 139-145, vol. 22.
Dropulic, et al., "A single amino acid change in the E2 glycoprotein of *Sindbis virus* confers neurovirulence by altering and early step of virus replication", J Virol, 1997, pp. 6100-6105, vol. 71(8).
Fazakerley, et al., "Replication of the A7(74) Strain of *Semliki Forest virus* is Restricted in Neurons", Virology, 1993, pp. 627-637, vol. 195(2).
Fothergill, et al., N Engl J Med, 1938, p. 41, vol. 219(12).
Frolova, et al., "Roles of Nonstructural Protein nsP2 and Alpha/Beta Interferons in Determining the Outcome of *Sindbis virus* Infection", J Virolg, Nov. 2002, pp. 11254-11264, vol. 76(22).
Glitner and Shahan, N Amer Vet, 1933, pp. 25-27, vol. 14.
Grieder, et al., Virology, 1995, pp. 994-1006, vol. 206(2).
Grimstad, Adv Virus Res, 1983, pp. 357-438, vol. 28.
Heil, et al., "An Amino Acid Substitution in the coding Region of the E2 Glycoprotein Adapts *Ross River Virus* to Utilize Heparan Sulfate as an Attachment Moiety", J Virol, Jul. 2001, pp. 6303-6309, Vol. 75.
Klimstra, et al., "Adaptation of *Sindbis virus* to BHK Cells Selects for Use of Heparan Sulfate as an Attachement Receptor", J Virol, Sep. 1998, pp. 7357-7366, vol. 72(9).
Lustig, et al., "Molecular basis of *Sindbis virus* neurovirulence in mice", J Virol, Jul. 1988, pp. 2329-2336, vol. 62 (7).
McKnight, et al., "Deduced consensus sequence of *Sindbis virus* strain AR339: mutations contained in laboratory strains which affect cell culture and in vivo phenotypes", J Virol, Mar. 1996, pp. 1981-1989, vol. 70(3).

(Continued)

*Primary Examiner* — Marcia S Noble
*Assistant Examiner* — Magdalene Sgagias

(57) ABSTRACT

The present invention discloses a chimeric alphavirus comprising a Sindbis virus cDNA fragment, an Eastern equine encephalitis virus cDNA fragment, a Western equine encephalitis virus cDNA fragment or a combination thereof. The present also discloses the use of this chimeric alphavirus as vaccines and in serological and diagnostic assays.

7 Claims, 9 Drawing Sheets

(56) References Cited

OTHER PUBLICATIONS

Paessler, et al., "Recombinant *Sindbis/Venezuelan equine encephalitis virus* is Highly Attenuated and Immunogenic", J Virol, Sep. 2003 pp. 9278-9286, Vol. 77(17).

Paessler, et al., "Replication and Clearance of *Venezuelan equine encephalitis virus* from the Brains of Animals Vaccinated with Chimeric SIN/VEE Viruses", J Virol, Mar. 2006, pp. 2784-2796, vol. 80(6).

Polo & Johnston, "Attenuating mutations in glycoproteins E1 and E2 of *Sindbis virus* produce a highly attenuated strain when combined in vitro", J Virol, Sep. 1990, pp. 4438-4444, vol. 64(9).

Powers, et al., Proc Natl Acad Sci., 1996, pp. 4187-4191, vol. 93.

Powers, et al., "The Use of Chimeric *Venezuelan equine encephalitis viruses* as an Apprach for the Molecular Identification of Natural Virulence Determinants", J Virol, May 2000, pp. 4258-4263, Vol. 74(9).

Scott and Weaver, Adv Virus Res., 1989, pp. 277-328, vol. 37.

Sharpe, et al., "Role of abortive retroviral infection of neurons in spongiform CNS degeneration", Nature, 1990, pp. 181-183, vol. 346(6280).

Shope, Am J Epidemiol, 1966, pp. 467-477, vol. 84(3).

Spotts, et al., "Resistance to Alpha/Beta Interferons Correlates with the Epizootic and Virulence Potential of *Venezuelan equine ecephalitis viruses* and is Determined by the 5' Noncoding Region and Glycoproteins", J Virol, 1998, pp. 10286-10291, vol. 72(12).

Strauss & Strauss, "The Alphaviruses: Gene Expression, Replication, and Evolution", Microbiol Rev., 1994a, pp. 491-562, vol. 58(3).

Swoveland and Johnson, Virology, 1989, pp. 131-138, vol. 170(1).

Tucker & Griffin, "Mechanism of altered *Sindbis virus* neurovirulence associated with a single-amino-acid change in the E2 Glycoprotein", J Virol, Mar. 1991, pp. 1551-1557, Vol. 65(3).

Tucker, et al., "Viral determinants of age-dependent virulence of *Sindbis virus* for mice", J Virol, 1993, pp. 4605-4610, vol. 67(8).

Tuittila & Hinkkanen, "Amino acid mutations in the replicase protein nsP3 of *Semliki Forest virus* cumulatively affect neurovirulence", J Gen Virol, 2003, pp. 1525-1533, vol. 84.

Tuittila, et al., "Replicase Complex Genes of *Semliki Forest virus* confer Lethal Neurovirulence", J Virol, 2000, pp. 4579-4589, vol. 74(10).

Vogel, et al., Am J Pathol, 2005, pp. 159-171, vol. 166(1).

Wang, et al., "Genetic and Phenotypic Changes Accompanying the Emergence of Epizootic Subtype IC *Venezuelan equine encephalitis viruses* from an Enzootic Subtype ID Progenitor", J Virol, May 1999, pp. 4266-4271, vol. 73(5).

Weaver, et al., Arch Virol Suppl, 2004, pp. 43-64, vol. 18.

White, et al., "Role of Alpha/Beta Interferon in *Venezuelan equine encephalitis virus* Pathogensis: Effect of an Attenuating Mutation in the 5' Untranslated Region", J Virol, Apr. 2001, pp. 3706-3718, Vol. 75(8).

\* cited by examiner

■ WEEV  ■ SINV AR339  □ EEEV

1306.SIN/C<sub>EEE-WEE</sub>/WEEV(McMillan)

Fig. 12

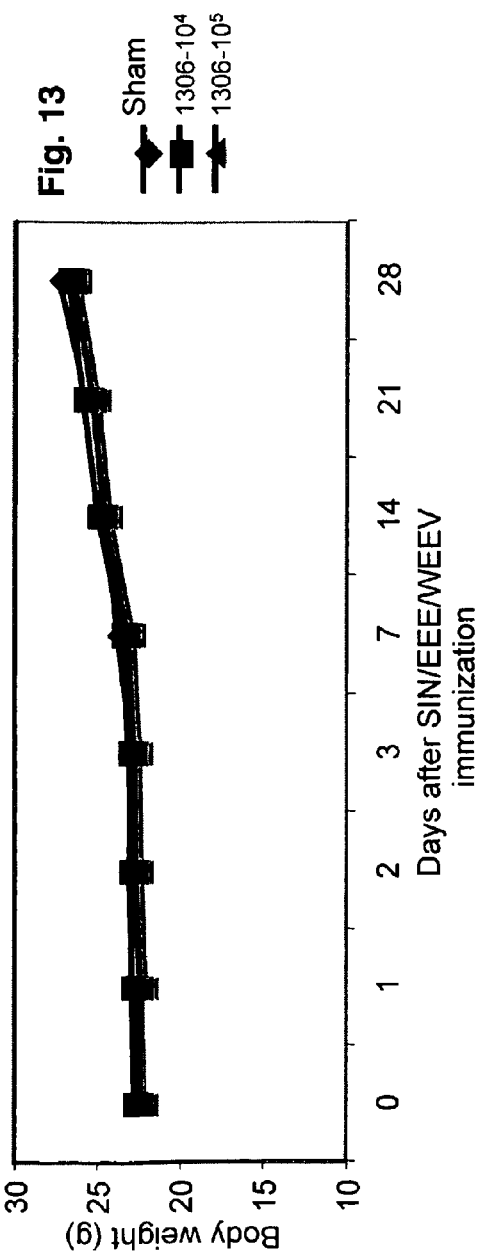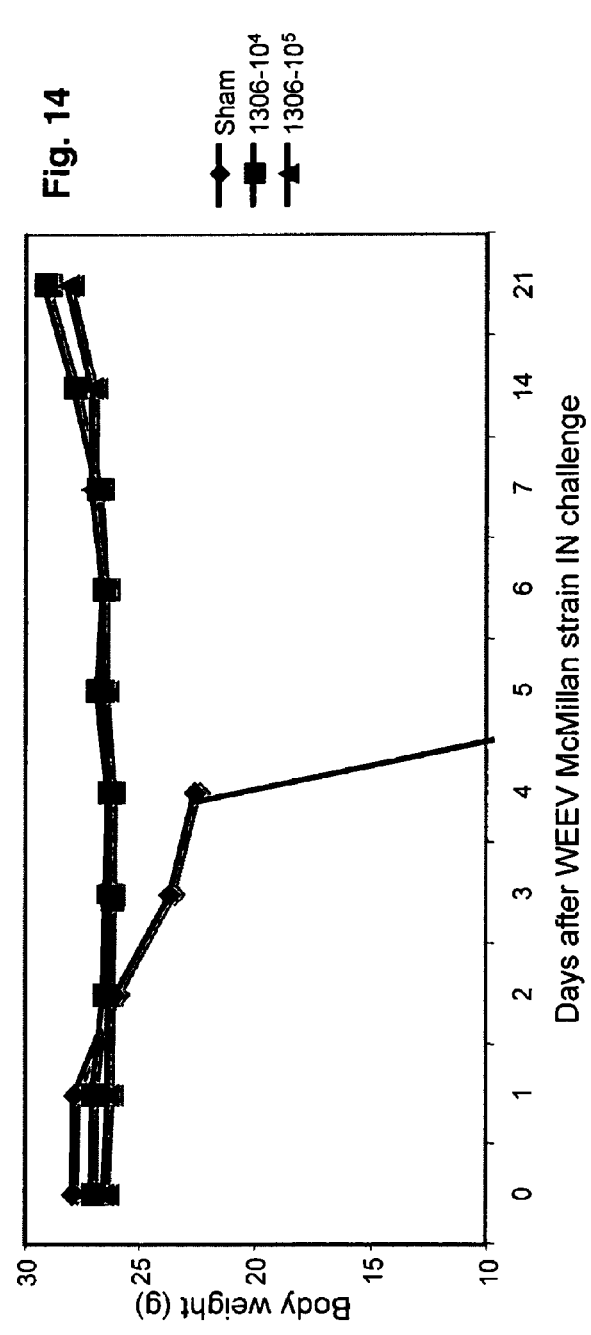

CHIMERIC SINDBIS-WESTERN EQUINE ENCEPHALITIS VIRUS AND USES THEREOF

CROSS REFERENCE TO RELATED APPLICATION

This non-provisional application claims benefit of provisional application U.S. Ser. No. 60/923,987 filed on Apr. 17, 2007, now abandoned.

FEDERAL FUNDING LEGEND

This invention was produced in part using funds obtained through an award U54 AI057156 from the National Institute of Allergy and Infectious Disease. Consequently, the federal government has certain rights in this invention.

BACKGROUND OF THE INVENTION

1. Field of the Invention

The present invention relates to the fields of molecular biology, virology and immunology. More specifically, the present invention provides an attenuated recombinant chimeric sindbis-western equine encephalitis virus (WEEV) and discloses its use as vaccines and in serological and diagnostic assays.

2. Description of the Related Art

Western equine encephalitis virus (WEEV) is not as neuroinvasive as Eastern equine encephalitis virus (EEEV). However, its transmission and pathogenesis are similar. Mosquitoes carry the virus from the wild bird reservoir to the dead-end hosts, horses and humans. Female mosquitoes acquire the virus by taking a blood meal from an infected host. The virus infects the epithelial cells of the midgut of the mosquito and spreads through the circulation to the salivary glands where it sets up a persistent infection. The virus enters a new host when the mosquito regurgitates virus-containing saliva into the victim's bloodstream. The virus replicates in the capillary endothelial cells, macrophages, monocytes, liver, spleen or lymphatic tissue.

Systemic symptoms (chills, fever, myaglia) occur at this time, perhaps due to production of interferon. A secondary viremia follows the replication in the reticuloendothelial system and allows infection of the target cells in the brain. Damage is due both to cell death following infection and to inflammation. The disease occurs only in months when mosquitoes are active. Subclinical infections greatly exceed the number of clinical cases. Although many infections do not progress beyond the systemic phase, infection of the brain (signaled by severe headache and nausea) is followed by a rapidly progressive downhill course. Although a vaccine has been developed for horses, this vaccine is not useful for the general population. Hence, it is necessary to develop vaccines that can be used for the general population since infants are particularly susceptible to CNS disease caused by this virus and survivors may have severe CNS sequelae.

Thus, prior art is deficient in vaccines that can be used to treat and/or prevent an individual from infection caused by western equine encephalitis virus. The present invention fulfills this long-standing need and desire in the art.

SUMMARY OF THE INVENTION

In one embodiment of the present invention, there is provided a recombinant DNA encoding a chimeric Western equine encephalitis virus (WEEV) comprising a Sindbis virus cDNA fragment, an Eastern equine encephalitis virus cDNA fragment, the Western equine encephalitis virus cDNA fragment or a combination thereof. In a further related embodiment of the present invention, there is an in-vitro synthesized viral RNA genome encoding the chimeric Western equine encephalitis virus described herein, a host cell comprising the viral RNA genome and an attenuated western equine encephalitis virus comprising the DNA described herein.

In yet another related embodiment of the present invention, there is provided a pharmaceutical composition comprising the above-mentioned attenuated Western equine encephalitis virus and a pharmaceutically acceptable carrier. In a related embodiment of the present invention, there is provided an immunogenic composition comprising a live attenuated western equine encephalitis virus vaccine, where the vaccine comprises the attenuated western equine encephalitis virus described herein.

In another related embodiment of the present invention, there is provided a method of protecting an individual from infections resulting from exposure to Western equine encephalitis virus. Such a method comprises administering a immunologically effective amount of the immunogenic composition comprising the live attenuated Western equine encephalitis virus vaccine described herein, where the vaccine elicits an immune response against the Western equine encephalitis virus in the individual, thereby protecting the individual from the infection.

In a further related embodiment of the present invention, there is provided an immunogenic composition comprising an inactivated vaccine, where the vaccine comprises the attenuated Western equine encephalitis virus described herein that is inactivated.

In yet another related embodiment of the present invention, there is provided a method of protecting an individual from infections resulting from exposure to Western equine encephalitis virus. This method comprises administering a immunologically effective amount of the immunogenic composition comprising the inactivated western equine encephalitis virus vaccine described herein, where the vaccine elicits an immune response against the western equine encephalitis virus in the individual, thereby protecting the individual from the infection.

In still yet another embodiment of the present invention, there is provided a method of determining the presence of an antibody to western equine encephalitis virus in a subject. Such a method comprises obtaining serum sample from the subject and performing assay using the attenuated western equine encephalitis virus described herein to determine presence or absence of antigenic reactions, effect of physical properties of the western equine encephalitis virus or a combination thereof in the serum sample, thereby determining the presence of the antibody to western equine encephalitis virus in the subject.

In another embodiment of the present invention, there is provided a method of determining the presence of an antibody to western equine encephalitis virus in a subject. This method comprises obtaining serum sample from the subject and performing assay using an inactivated western equine encephalitis virus, where the inactivated western equine encephalitis virus comprises the attenuated western equine encephalitis virus described herein that is inactivated to determine presence or absence of antigenic reactions, effect of physical properties of the western equine encephalitis virus or a combination thereof in the serum sample, thereby determining the presence of the antibody to western equine encephalitis virus in the subject.

In yet another embodiment of the present invention, there is provided a kit. Such a kit comprises the attenuated Western equine encephalitis virus described herein, the attenuated Western equine encephalitis virus described herein that is inactivated or combinations thereof.

BRIEF DESCRIPTION OF THE DRAWINGS

FIG. 2 shows a replication of VEEV, eastern equine encephalitis virus and western equine encephalitis virus in vitro.

FIGS. 3A-3C show replication of the chimeras. FIG. 3A compares the number of plaque forming (infectious) units of SIN/WEEV passaged on BHK and Vero cells. FIG. 3B shows electrophoresis of the virus on SDS polyacrylamide gel. FIG. 3C shows electrophoresis of radiolabeled RNA from infected BHK and Vero cells.

FIG. 4 shows survival of vaccinated mice after intranasal western equine encephalitis virus challenge.

FIG. 5 shows body temperatures after SIN/western equine encephalitis virus vaccination.

FIG. 6 shows body weight after SIN/western equine encephalitis virus vaccination.

FIG. 7 shows body temperatures of mice subjected to immunization and challenge.

FIG. 8 shows virus titers in vaccinated mice 3 days after intraperitoneal western equine encephalitis virus challenge (N=2).

FIG. 9 shows survival of six-day old NIH Swiss mice infected intracranially with SIN/western equine encephalitis virus.

FIG. 10 shows virus replication in brains of six-day old mice infected intracranially with western equine encephalitis virus or SIN/western equine encephalitis virus.

FIG. 11 shows a schematic representation of the SIN/$C_{EEE-WEE}$/WEEV viral genome.

FIG. 12 shows replication of SINV Toto 1101 and SIN/$C_{EEE-WEE}$/WEEV in Vero cells. Cells were infected at a MOI of 10 PFU/cell. Media was replaced at the indicated time points and titers assessed on BHK-21 cells.

FIG. 13 shows weight gain in 6-week old mice after vaccination with the indicated dose of SIN/EEE/WEEV or after sham vaccination.

FIG. 14 shows weight change in 10-week old vaccinated or sham-vaccinated mice after intranasal challenge ($10^5$ PFU) with McMillan strain of WEEV or after sham vaccination.

DETAILED DESCRIPTION OF THE INVENTION

Figure 1:
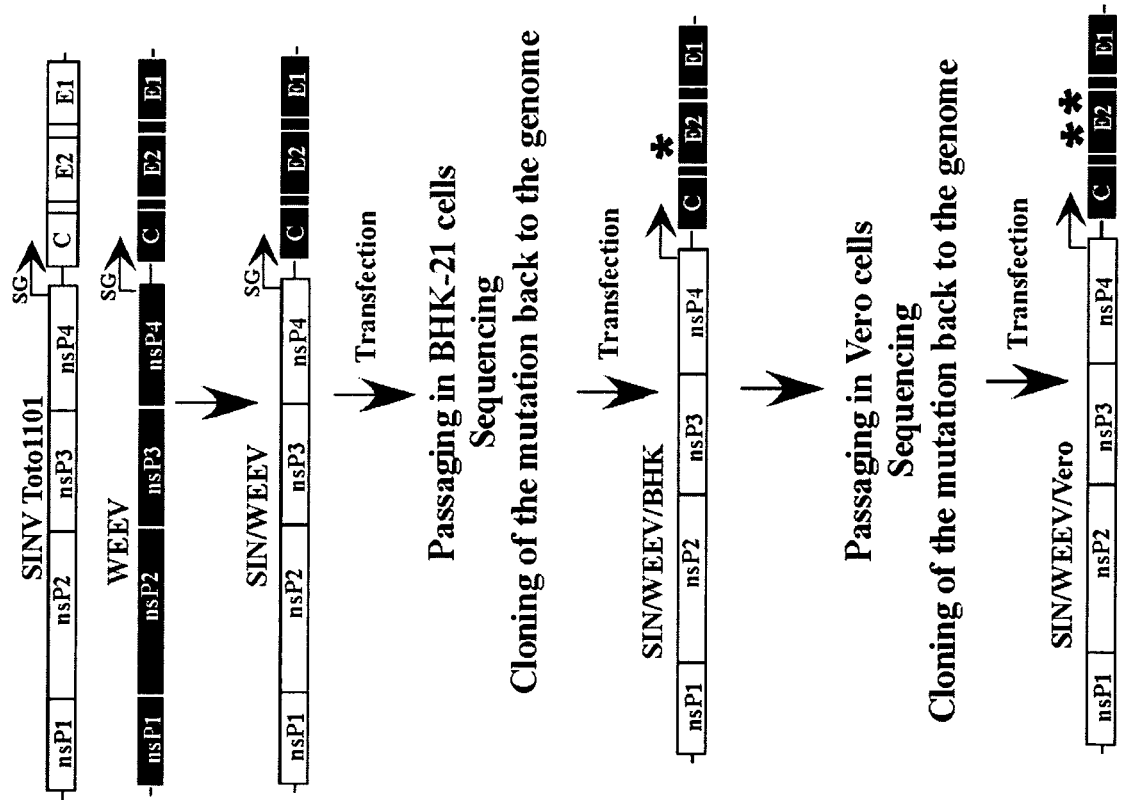
FIG. 1 shows a schematic representation of selection procedure used herein.

The present invention discloses construction of chimeric Sindbis-western equine encephalitis virus. Briefly, infectious cDNA clones encoding chimeric alphaviruses have been developed for use as live attenuated vaccine strains and as diagnostic reagents. These strains include the cis-acting sequences from the 5' and 3' termini of the Sindbis virus genome as well as the 26S promoter and non-structural protein genes. The structural protein genes were derived from 3 strains of western equine encephalitis virus. The strains western equine encephalitis virus may include but are not limited to CO92-1356. The chimeric alphaviruses of the present invention use a completely different strategy for attenuation (chimeric engineering using a Sindbis virus-derived backbone and cis-acting sequence elements) from the previously described alphavirus strains.

Although the recombinant chimeric viruses disclosed herein were identical in their protein content to the wild type western equine encephalitis virus, these chimeric viruses were highly attenuated in the mouse model for human and equine disease. The recombinant chimeric viruses elicited immune responses like the wild-type western equine encephalitis virus strains and reacted identically in antibody assays. Thus, the chimeric viruses disclosed herein may be used for vaccination of humans or domestic animals to protect against infections resulting from natural exposure or from bioterror attack. They may also be used as surrogates for wild type western equine encephalitis virus in serological and diagnostic assays. Since these surrogates can be handled at biosafety level 2, the use of these surrogates will dramatically improve efficiency and safety in diagnostic laboratories and vaccine production facilities.

The narrowest application of the above-disclosed chimeric viruses is its use as live-attenuated vaccines or as formalin-inactivated western equine encephalitis virus in humans or domestic animals. The inactivation of wild-type, virulent western equine encephalitis virus is technically challenging and the presence of live virus in a vaccine can result in encephalitis in a vaccinated animal. The chimeras discussed herein will be cheaper to produce and safer to use even if inactivation is incomplete. Further, use of the vaccine in live form will allow a single dose vaccination for faster and longer lasting immunity (probably life-long; in contrast to the current vaccine requires multiple, initial doses and semi-annual boosting to maintain protective immunity in horses). Additionally, an equine vaccine may substitute the instantly claimed chimeric viruses into their production protocol without any methodological changes.

Broader applications may include experiments or assays that measure antigenic reactions or other physical properties of western equine encephalitis virus particles since these chimeric virions have the same protein make-up and structure as the wild type western equine encephalitis virus. Such assays may include but are not limited to serological assays such as plaque reduction neutralization tests, enzyme linked immunosorbent assays, hemagglutination inhibition and complement fixation assays conducted with live or inactivated antigens produced from the chimeras, production of virus for inactivation using formalin for vaccination of humans or animals and structural studies employing methods such as electron microscopy.

The present invention also discloses chimeric Western equine encephalitis virus that comprise Sindbis virus cDNA fragment, Eastern equine encephalitis cDNA fragment and Western equine encephalitis virus cDNA fragment. The Western equine encephalitis virus cDNA fragment in this case was derived from McMillan strain of Western equine encephalitis virus and the Eastern equine encephalitis virus cDNA fragment was derived from NA strain FL93-939.

The list of mutations, identified in the subgenomic RNA of McMillan strain of WEEV, compared to the GeneBank sequence. This particular strain (plaque purified variant) was used for designing the SIN/WEEV chimeras.

1007 a→c 336 Q→P
1178 t→a 393 V→D
1198 a→g 400 K→E
1303 g→a 435 A→T
1760 c→t 587 A→V
2238 g→a
2385 g→a
2675 c→t 892 S→F
2709 g→a
2977 a→g 993 R→E 2978 g→a 993 R→E
3372 c→t
3531 c→t
3552 t→a

The particular problem with the chimeras, having WEEV glycoproteins, is that infectivity of viruses is 20-50-fold higher on BHK-21 cells than on Vero cells. Nevertheless, all of the experiments were done on Vero, because this will most likely be a cell line of choice for virus production. The following were the virus combinations that were tried:

1301. SIN/WEEV encoded all of the structural proteins of WEEV McMillan strain. It is viable virus, but titers were below the level than was expected. It was passaged 10 times on Vero cells, but titers remained at the level of $3 \times 10^5$ PFU/ml. Thus, there was no reasonable adaptation, and the experiments were discontinued.

1303. SIN/$C_{SIN-WEE}$/WEEV encodes McMillan strain-specific glycoproteins and carboxy-terminal fragment of capsid. The amino-terminal domain of capsid, encoding the RNA-binding domain was derived from SINV. This virus replicates to the titers $7-10 \times 10^6$ PFU/ml in Vero cells even in serum-free medium. These titers are equivalent to $2-4 \times 10^8$ PFU/ml, if the same samples are plaqued on BHK-21 cells.

1305. SIN/$C_{SIN}$/WEEV encodes McMillan-specific glycoproteins, and the entire capsid was derived from SINV. This variant was incapable of growing to the titers higher than $4 \times 10^5$ PFU/ml in Vero cells. Therefore, the experiments with this recombinant were discontinued.

1306. SIN/$C_{EEE-WEE}$/WEEV encodes McMillan strain-specific glycoproteins and carboxy-terminal fragment of capsid. The amino-terminal domain of capsid, encoding the RNA-binding domain was derived from EEEV NA strain Florida93. The rationale for using the EEEV-specific capsid fragment was based on previous studies, which demonstrated that EEEV capsid is highly efficient in packaging SINV genome. The designed recombinant virus replicated in Vero cells to the titers $2-3 \times 10^7$ PFU/ml. This virus was additionally passaged 3 times on Vero cells (no increase in titers was detected) and then used for infecting mice.

Although the present invention has generated chimeric virus strains that comprise western equine encephalitis virus, the same technical principles as discussed herein may be applied to construct chimeric virus strains that comprise other alphaviruses (Venezuelan equine encephalitis virus (VEEV) or Eastern equine encephalitis virus (EEEV)) or other related viruses. Furthermore, although the present invention used the McMillan strain of Western equine encephalitis virus to generate these chimeric virus strains, one of skill in the art may use similar virulent strain of Western equine encephalitis virus to generate such chimeric viruses. If modified accordingly, these chimeric viruses may then be utilized in the same way as is discussed for the chimeras of the present invention.

The present invention is directed to a recombinant DNA encoding a chimeric Western equine encephalitis virus comprising a Sindbis virus cDNA fragment, an Eastern equine encephalitis virus cDNA fragment, the western equine encephalitis virus cDNA fragment or a combination thereof. Specifically, the Sindbis virus cDNA fragment comprises cis-acting sequences from the 5' and 3' termini, 26S promoter and nonstructural protein genes while the western equine encephalitis virus cDNA fragment comprises structural protein genes. The structural genes of Western equine encephalitis virus may encode envelope glycoprotein, carboxy-terminal of capsid protein or both. Representative examples of the strains of western equine encephalitis virus from where the cDNA fragment is derived may include but is not limited to the CO92-1356 strain, the McMillan strain or both. Additionally, the recombinant DNA may include Eastern equine encephalitis virus capsid protein genes. The capsid protein gene of the Eastern equine encephalitis virus may encode the amino-terminal domain of capsid protein. Representative examples of the strains of Eastern equine encephalitis virus from where the cDNA fragment is derived may include but is not limited to NA strain FL93-939. Furthermore, the chimeric DNA may encode structural glycoproteins that are identical to wild-type western equine encephalitis virus.

The present invention is also directed to an in-vitro synthesized viral RNA genome encoding the chimeric Western equine encephalitis virus described herein, a host cell comprising the viral genome and an attenuated western equine encephalitis virus comprising the recombinant DNA described herein. The present invention is further directed to a pharmaceutical composition comprising the attenuated western equine encephalitis virus described supra and a pharmaceutically acceptable carrier.

The present invention is still further directed to an immunogenic composition comprising a live attenuated western equine encephalitis virus vaccine, where the vaccine comprises the attenuated western equine encephalitis virus described herein.

The present invention is also directed to a method of protecting an individual for infections resulting from exposure to Western equine encephalitis virus, comprising administering a immunologically effective amount of an immunogenic composition comprising the live attenuated western equine encephalitis virus vaccine described herein, where the vaccine elicits an immune response against the western equine encephalitis virus in the individual, thereby protecting the individual from the infection. Additionally, the individual that may benefit from such a treatment is a human or a domestic animal.

Alternatively, the present invention is directed to an immunogenic composition comprising an inactivated western equine encephalitis virus vaccine, where the vaccine comprises the attenuated western equine encephalitis virus described herein, where the attenuated western equine encephalitis virus is inactivated.

The present invention is also directed to a method of protecting an individual for an infection resulting from exposure to Western equine encephalitis virus, comprising administering a immunologically effective amount of the immunogenic composition comprising the inactivated western equine encephalitis virus vaccine described herein, where the vaccine elicits an immune response against the western equine encephalitis virus in the individual, thereby protecting the individual from infection. Additionally, the individual that may benefit from such a treatment is a human or a domestic animal. Generally, the infection may arise due to natural exposure or from a bioterror attack.

The present invention is further directed to a method of determining the presence of an antibody to Western equine encephalitis virus in a subject, comprising: obtaining a serum sample from the subject, and performing an assay using the attenuated virus described herein to determine the presence or absence of antigenic reactions, effect on physical properties of the western equine encephalitis virus or a combination thereof in the serum sample, thereby determining the presence of antibody to western equine encephalitis virus in the subject. Examples of such assays are not limited to but may include enzyme linked immunosorbent assays, hemagglutination inhibition assay, complement fixation assay or plaque reduction neutralization assay. Additionally, the serum may be obtained from a human or a domestic animal.

Alternatively, the present invention is further directed to a method of determining the presence of an antibody to western equine encephalitis virus in a subject, comprising: obtaining a serum sample from the subject, and performing assay using an inactivated western equine encephalitis virus, where the inactivated western equine encephalitis virus comprises the attenuated virus described herein that is inactivated to determine the presence or absence of antigenic reactions, effect on physical properties of the western equine encephalitis virus or a combination thereof in the serum sample, thereby determining the presence of antibody to western equine encephalitis virus in the subject. All other aspects regarding the type of assays and the subject is as discussed supra.

The present invention is still further directed to a kit comprising: an attenuated western equine encephalitis virus described herein, an attenuated western equine encephalitis virus described herein that is inactivated or combinations thereof. Furthermore, the kit may also comprise attenuated and/or inactivated forms of other related chimeric viruses (VEEV, eastern equine encephalitis virus or any related viruses) that are constructed based on the same principles as discussed herein.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

The composition described herein can be administered independently, either systemically or locally, by any method standard in the art, for example, subcutaneously, intravenously, parenterally, intraperitoneally, intradermally, intramuscularly, topically, or nasally. Dosage formulations of the composition described herein may comprise conventional non-toxic, physiologically or pharmaceutically acceptable carriers or vehicles suitable for the method of administration and are well known to an individual having ordinary skill in this art.

The composition described herein may be administered independently one or more times to achieve, maintain or improve upon a therapeutic effect. It is well within the skill of an artisan to determine dosage or whether a suitable dosage of the composition comprises a single administered dose or multiple administered doses. An appropriate dosage depends on the subject's health, the induction of immune response and/or prevention of infection caused by western equine encephalitis virus, the route of administration and the formulation used.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Cells

Baby hamster kidney (BHK-21) and African green monkey (Vero) cells were purchased from the American Type Culture Collection (Bethesda, Md.) and grown at 37° C. in Eagles minimal essential medium (MEM) with 10% fetal bovine serum (FBS) and 0.05 mg/ml of gentamycin sulfate (Invitrogen, Carlsbad, Calif.). The *Aedes albopictus* mosquito cell line C7/10 was maintained in MEM at 32° C. with 10% FBS and 10% tryptose phosphate broth.

Example 2

Construction of Recombinant SIN/WEEV Plasmids

Chimeric alphavirus infectious cDNA clones were derived SINV strain AR339 (McKnight et al., 1996), and WEEV strain CO92-1356, a 1992 Colorado isolate from *Culex tarsalis* mosquitoes, was passed once in Vero cells prior to preparation of viral RNA from infected BHK-21 cells. The nonstructural protein genes as well as the cis-acting RNA elements were derived from SINV, and the structural protein genes were derived from western equine encephalitis virus. The 3' untranslated region contained 335 nucleotide sequences derived from SINV as well as the poly (A) tail, followed by either a Not I or other restriction site. The subgenomic RNAs of the chimeric viruses at their 5' ends contained 4 SINV-specific nts followed by the western equine encephalitis virus sequence (starting from nt 5 of western equine encephalitis virus subgenomic RNA). This subgenomic 5'UTR was designed to preserve the sequence of the promoter while maintaining the putative secondary structure that might be required for efficient western equine encephalitis virus structural protein translation.

Example 3

In Vitro Transcription, Transfection and Production of Infectious Virus

Plasmid DNA was linearized by restriction endonuclease digestion with Not I and purified by phenol-chloroform extraction and ethanol precipitation. RNA was synthesized in vitro in the presence of Cap analog by SP6 RNA polymerase in the conditions recommended by a manufacturer (Invitrogen) and examined on an ethidium bromide-containing agarose gel to determine yield and integrity of the transcripts. The RNA was then transfected into BHK-21 cells by electroporation. The rescued viruses were collected following the development of cytopathic effects (CPE) at approximately 24 h post-transfection. Virus titers were determined by plaque assay on Vero cells.

Example 4

Virus Replication in Cell Cultures

Replication kinetics of SINV and the chimeric viruses were compared in Vero and C7/10 cells. Confluent monolayers grown in 12-well plates were infected at a multiplicity of infection (MOI) of 1 PFU/cell at 37° C. for Vero cells and 32° C. for C7/10 cells. Each virus was infected in triplicate for statistical analysis. After 1 h of incubation, the plates were washed with phosphate buffer saline (PBS) and 2 ml of EMEM with 2% FBS were added. At selected times postinfection, cell culture medium was collected and replaced with fresh medium. Virus titers in the harvested media were determined by plaque assay on Vero cells.

Example 5

Mouse Infections

Six- to 8-week-old female and older pregnant NIH Swiss mice were purchased from Harlan (Indianapolis, Ind.) and maintained under specific-pathogen-free conditions. Newborn mice were held for 6 days after birth prior to intracerebral infection.

Adult mice were vaccinated subcutaneously (SC) in the medial thigh in a total volume of 100 μl of PBS. Blood samples were collected from the retroorbital sinus and virus titers were determined by plaque assay. To monitor body temperature, some adult mice were anaesthetized before infection with isofluorane and implanted SC with a pre-programmed telemetry chip (IPTT-300; Bio Medical Data Systems, Inc., Seaford, Del.) according manufacturer's instructions. Mice were monitored for 7-10 days to ensure that trauma, infection, or other reactions to the implanted chips. Temperatures and body weights were recorded daily without anesthetization.

Parental viruses (sindbis or western equine encephalitis virus) and the sindbis/western equine encephalitis virus chimeras were also inoculated into 6-day-old NIH Swiss mice at a dose of 5.3 $\log_{10}$ PFU by the intracerebral (IC) route. Animals were monitored daily for 28 days for signs of paralysis or ataxia associated with western equine encephalitis virus. Two animals per group were sacrificed on days 1 and 2 and virus content in the brains was determined by plaque assay. Intranasal infection of adult mice was done using a total volume of 20 μl of PBS (10 μl per nostril).

Example 6

Serological Assays

Neutralizing antibodies were assayed using 80% plaque reduction neutralization tests (PRNT) with the parental CO92-1356 strains of western equine encephalitis virus (Beaty et al., 1989).

Example 7

Replication of Chimeric Viruses and Adaptation in Cell Cultures

Figure 2:
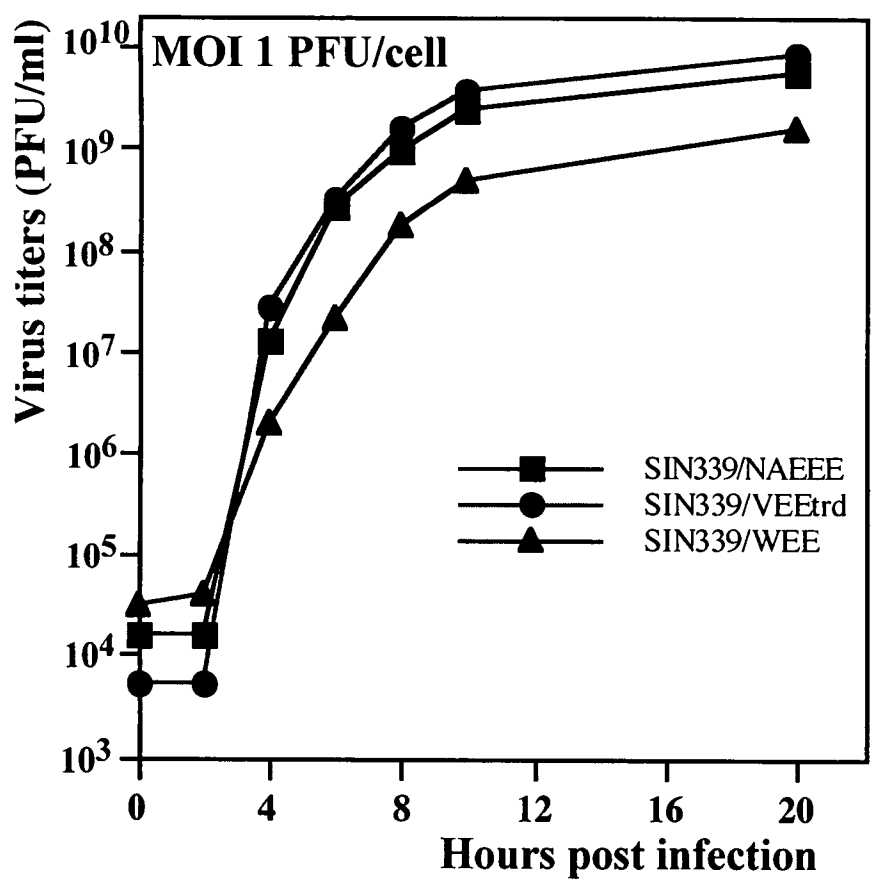
Figures 3A, 3B, 3C:
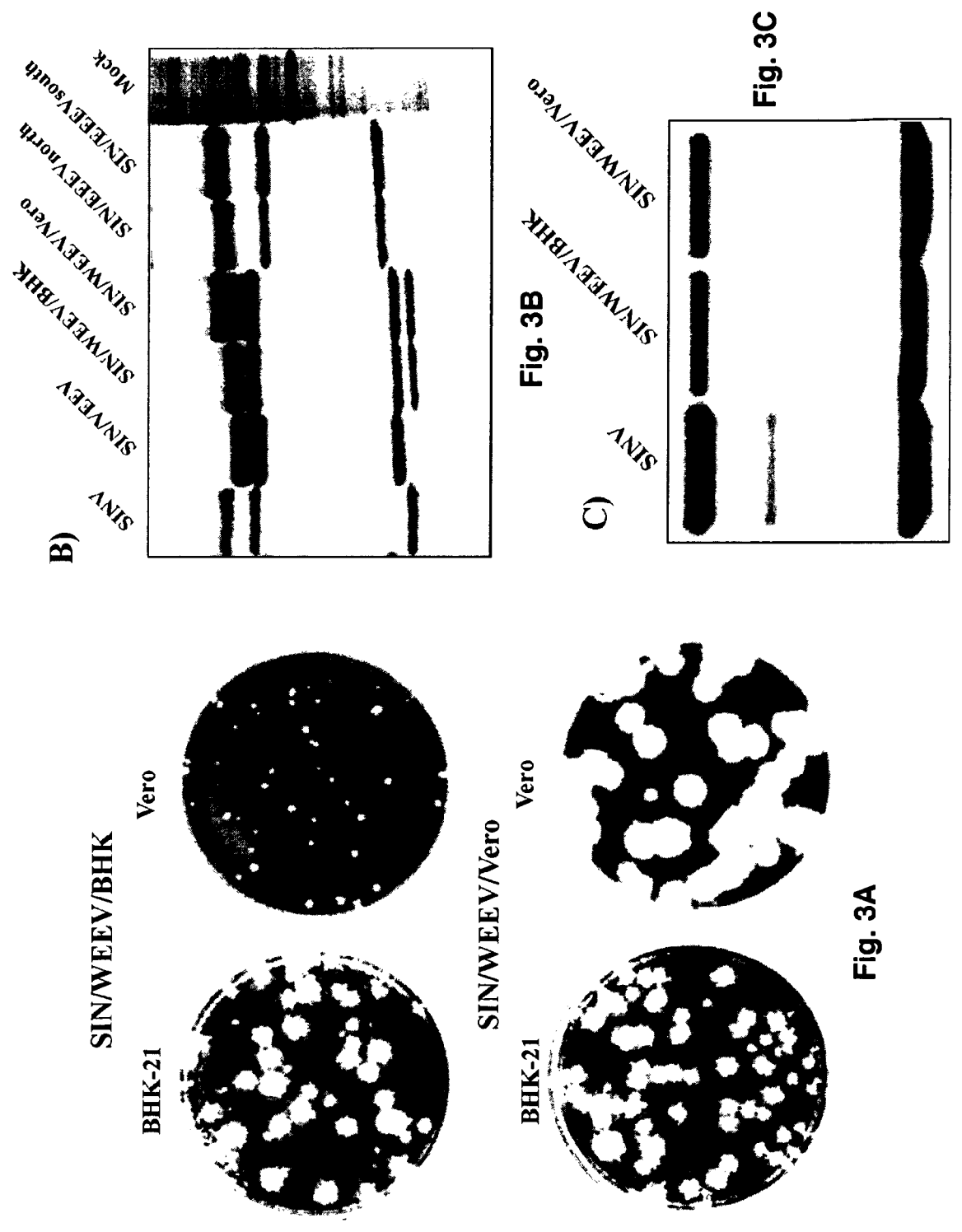

The overall design of chimeric SIN/western equine encephalitis virus cDNA infectious clones was essentially the same as that described previously for SIN/Venezuelan equine encephalitis virus (VEEV) chimeras (Paessler et al., 2003; Paessler et al., 2006). The chimeric virus recovered from BHK cells after RNA electroporation had a titer of only ca. $10^5$ PFU/m, suggesting impaired replication compared to typical wild-type alphaviruses. Therefore, this virus was passaged 5 times on BHK cells and tested again for replication efficiency, which increased to ca. $10^8$ PFU/ml (FIG. 1). Genomic sequencing of the adapted virus showed 2 nonsynonymous mutations that resulted in a his-to-leu change in the nsP3 and a glu-to-lys change in the E2 envelope glycoprotein. However, when these mutations were introduced into the chimeric cDNA clone, a small plaque size (FIG. 3A) and poor replication was observed in Vero (an approved mammalian vaccine substrate) cells. Therefore, the derived virus was passaged 5 times in Vero cells and resequenced, resulting in the detection of a lys-to-asn change in the E2 protein. This mutation was predicted to add an N-linked glycosylation site to the E2 protein. When placed into the cDNA clone, the mutation yielded a virus that produced larger plaque size on Vero cells (FIG. 3A) and that replicated efficiently at levels only slightly lower than other chimeric alphaviruses described previously (3) with peak titers of about $10^9$ PFU/ml (FIG. 2). Electrophoresis of virus on an SDS polyacrylamide gel confirmed the decreased mobility of the E2 protein, reflecting the additional glycosylation site (FIG. 3B). Electrophoresis of radiolabeled RNA from infected BHK and Vero cells showed the presence of large amounts of both genomic and subgenomic RNAs (FIG. 3C).

Example 8

Purification of Chimeric Viruses

Vero cells were infected at an MOI of 1 PFU/cell. After incubation for 5 h at 37° C., the FBS-containing media were discarded and cells were washed with PBS to remove residual FBS. Then incubation continued in the minimum volume of serum-free VP-SFM medium until the development of noticeable CPE. Before the complete destruction of the monolayer, media were harvested, diluted with 0.5 volumes of 0.01 M Tris-HCl pH=7.5 buffer (to reduce the concentration of NaCl to 0.1 M) and incubated with 0.1 volume of Heparin-Sepharose for 1 h at 4° C. with continuous shaking. Next, Sepharose was pelleted by a low-speed centrifugation and transferred to the column. Bound viruses were eluted using a three-step gradient of 0.2, 0.3 and 0.4 M NaCl in 0.01 M Tris-HCl pH=7.5 buffer. The results of the experiments are presented in Table 1.

TABLE 1

Column purification of chimeras

| Virus | VERO-stock | Super | 0.2M NaCl | 0.3M NaCl | 04M NaCl |
|---|---|---|---|---|---|
| SIN/NAEEE | 100% | 20% | 38% | 4% | 0.20% |
| SIN/WEE | 100% | 5% | 10% | 33% | 33% |
| SIN/VEE C7/10 | 100% | 30% | 56% | 12% | 2% |
| SIN/VEE BHK | 100% | 13% | 78% | 2% | 0.20% |

Example 9

Attenuation and Immunogenicity

To assess attenuation and safety of the SIN/WEEV chimera, 8-week-old, female NIH Swiss mice were inoculated SC with doses of 3.5-5.5 $\log_{10}$ PFU. Controls were sham-infected with PBS. Viremia was not detected in the serum by plaque assay, where the limit of detection was 8 PFU/ml. None of the animals infected at any dose exhibited any signs of disease. Four weeks after immunization, animal sera were collected to measure antibody responses. Antibody titers in sera collected 4 weeks after immunization and measured by PRNT showed a dose response to SIN/WEEV, with the highest mean titers and fraction of mice with detectable antibodies following immunization with 5.5 $\log_{10}$ PFU. At this dose, all mice seroconverted and the mean PRNT titer was 1:190 (Table 2).

TABLE 2

80% PRNT antibody titers against WEEV after immunization with SIN/WEEV

| | Vaccine dose | | |
|---|---|---|---|
| Mouse number | $3 \times 10^3$ PFU | $3 \times 10^4$ PFU | $3 \times 10^5$ PFU |
| 1 | 160 | <20 | 20 |
| 2 | 20 | 160 | 40 |

TABLE 2-continued

80% PRNT antibody titers against WEEV after immunization with SIN/WEEV

| Mouse number | Vaccine dose | | |
|---|---|---|---|
| | $3 \times 10^3$ PFU | $3 \times 10^4$ PFU | $3 \times 10^5$ PFU |
| | <20 | 20 | 40 |
| 3 | <20 | 20 | 40 |
| 4 | <20 | <20 | 160 |
| 5 | <20 | <20 | 320 |
| 6 | <20 | <20 | 160 |
| 7 | 40 | 80 | 160 |
| 8 | 40 | 20 | 320 |
| 9 | <20 | <20 | 640 |

Example 10

Protection Against WEEV Challenge

Protection against intranasal challenge with $10^6$ PFU the McMillan strain of western equine encephalitis virus, 4 weeks after immunization, also showed a vaccine dose response. Immunization with 3.3 and 4.3 $\log_{10}$ PFU of SIN/WEEV resulted in 40 and 50% protection, respectively, while the 5.3 $\log_{10}$ PFU dose provided 100% protection (FIG. 4) and no apparent disease. The mice that died after lower doses or sham vaccination developed signs of encephalitis including ruffled fur and hind limb paralysis.

Example 11

Body Temperature and Weight Changes Associated with Vaccination and Challenge

Figures 4, 5:
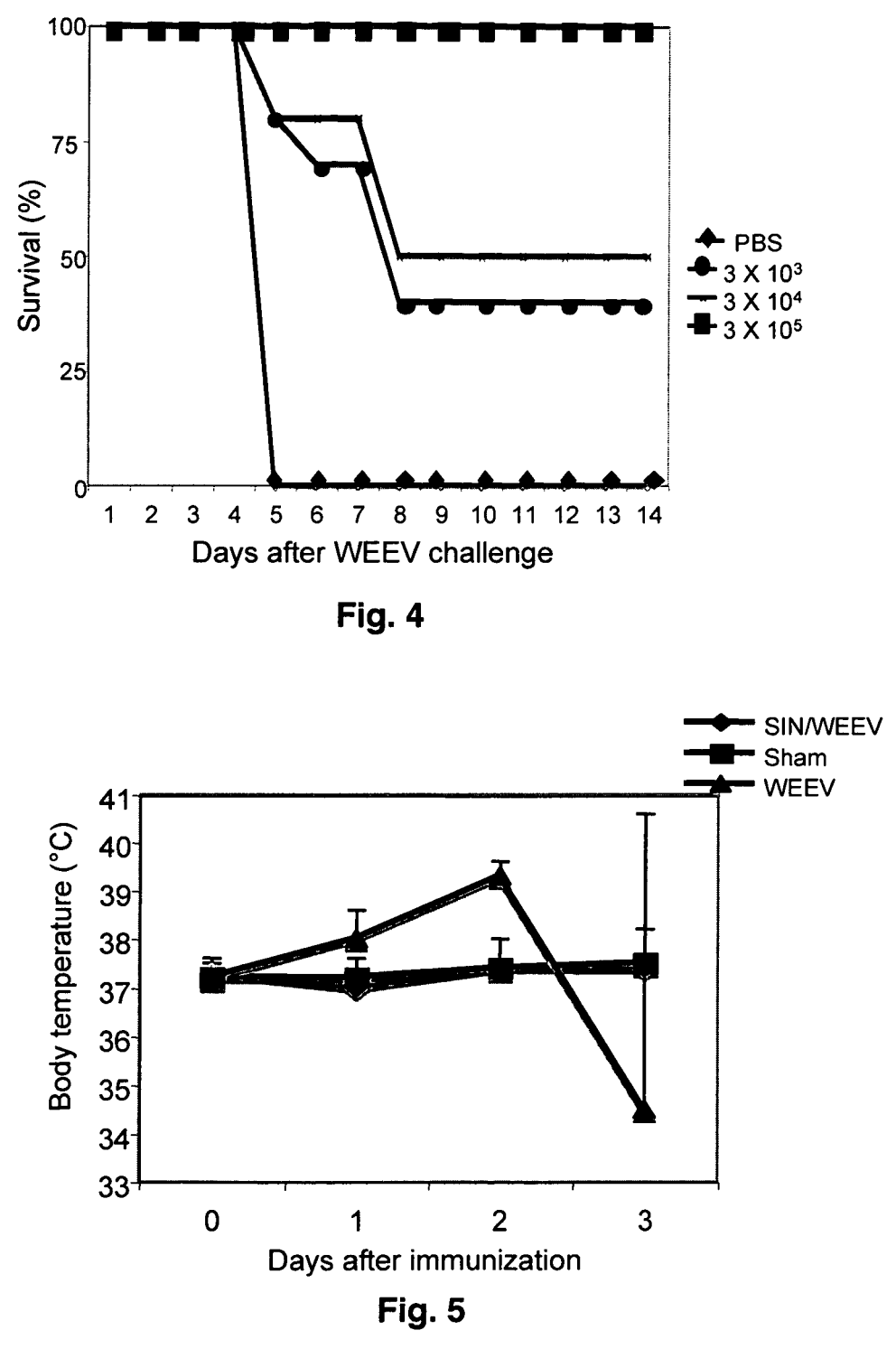

To monitor with greater sensitivity the potential clinical signs related to vaccination or challenge, randomly assigned cohorts of weight-matched, seven to 8-week-old mice were implanted with pre-programmed telemetry chips to measure body temperature before and after SC vaccination with 5.3 $\log_{10}$ PFU of SIN/WEEV. No febrile response was detected after vaccination or sham-vaccination (PBS), and all body temperatures remained within the normal range (35.5-38° C.). However, following infection with western equine encephalitis virus strain McMillan (positive control for virulence), mice exhibited an increase in mean body temperature beginning one day post-infection followed by a decline on day 3 (FIG. 5). Body weight also increased after vaccination (FIG. 6) but declined after western equine encephalitis virus infection (positive control for virulence).

Example 12

Challenge of Immunized Mice

Figures 6, 7:
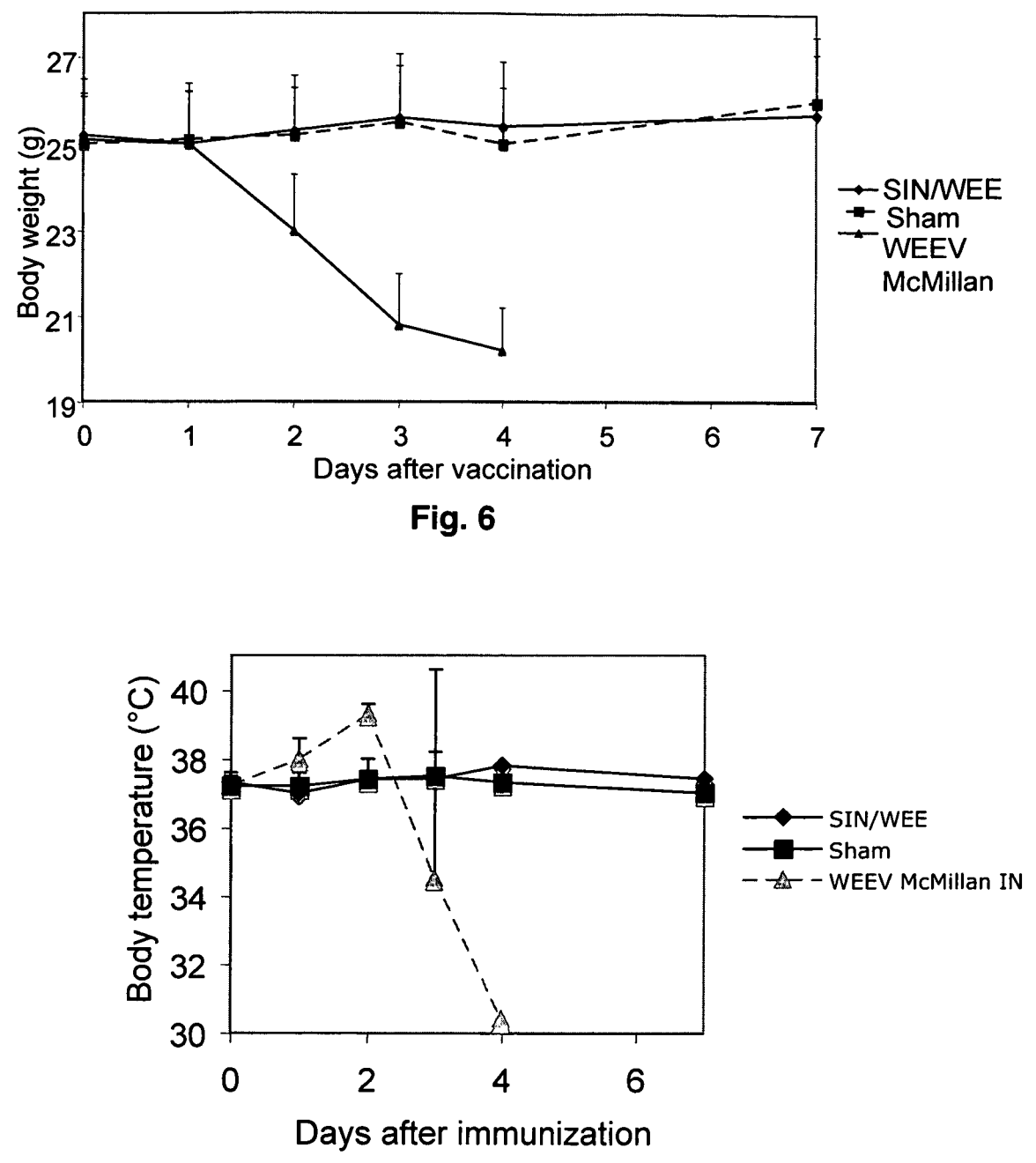

The immunized mice described above were challenged with western equine encephalitis virus at day 28 after vaccination. All sham-vaccinated mice developed clinical signs of encephalitis and died by day 7 post-challenge. These sham-vaccinated mice showed a febrile response by day 4 (FIG. 7). In contrast, mice vaccinated with SIN/WEEV and then challenged with western equine encephalitis virus showed no signs of disease, and none of the chimera-vaccinated mice exhibited a body temperature outside of the normal range (35.5-38° C.).

Example 13

Levels of Virus Replication in Immunized Mice after Challenge

The virus replication levels in organs of 12-week-old mice previously immunized with SIN/WEEV (5.3 $\log_{10}$ PFU) and challenged intraperitoneally with western equine encephalitis virus were examined. On day 3 after infection, vaccinated mice had no detectable western equine encephalitis virus in their brains, hearts, lungs, livers, spleens, and kidneys. In contrast, sham-vaccinated mice had large amounts of virus in their brains, with lesser amounts in the heart and spleen.

Example 14

Neurovirulence and Replication of Chimeric Vaccine Candidates in 6 Day-Old Mice

Figures 8, 9, 10:
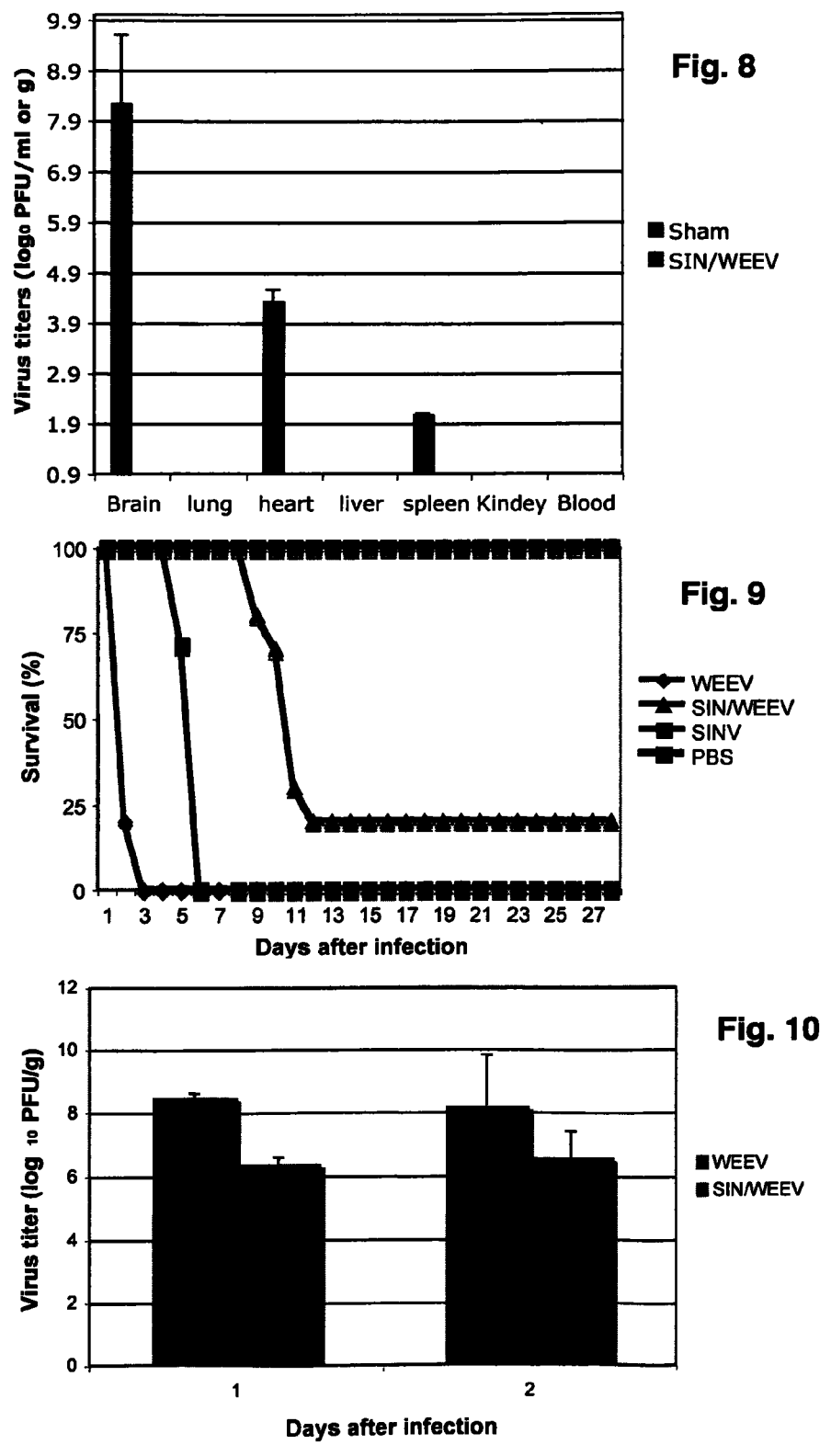

To use a highly stringent model for neurovirulence, cohorts of ten 6 day-old NIH Swiss mice were inoculated IC (5 $\log_{10}$ PFU) with either SINV/western equine encephalitis virus chimeras or the parental western equine encephalitis virus or SINV strains and monitored for signs of neurologic disease (FIG. 9). The CO92-1356 parental western equine encephalitis virus strain was highly neurovirulent, and all animals died within 3 days of infection. SINV strain AR339 was slightly less virulent, with all mice dying between days 5-6. In contrast, all mice infected with the SIN/western equine encephalitis virus strain survived until day 8, and 2 of the 10 mice survived until the experiment was terminated on day 28. This level of virulence is lower than that of the TC-83 live VEEV vaccine strain and is comparable to that described previously for other attenuated, Sindbis-based chimeric alphavirus vaccine candidates (Paessler et al., 2003; Paessler et al., 2006).

Levels of viral replication in the brains of the 6-day-old mice were quantified by plaque assay on days 1 and 2 after infection (FIG. 10). On day 1, the parental western equine encephalitis virus strain replicated to over 8 $\log_{10}$ PFU/g and the mean level of virus replication of the sindbis/western equine encephalitis virus chimeras was 100-fold lower. Virus titers were similar on day 2, with the sindbis/western equine encephalitis virus titers increasing slightly to a mean of 6.6 $\log_{10}$ PFU/g.

Example 15

Further Modification of the Chimeric Western Equine Encephalitis Virus

In an attempt to increase the immunogenicity of the SIN/WEEV vaccine candidate, a new chimera was designed to include the envelope glycoprotein genes from a more virulent WEEV strain called McMillan. SIN/$C_{EEE-WEE}$/WEEV (strain 1306) encodes McMillan strain-specific glycoproteins and carboxy-terminal fragment of capsid. The amino-terminal domain of capsid, encoding the RNA-binding domain was derived from EEEV NA strain Florida93 (FIG. 11). The rationale for using the EEEV-specific capsid fragment was based on the previous studies, which demonstrated that EEEV capsid is highly efficient in packaging SINV genome. The designed recombinant virus replicated in Vero cells to the titers 2-3×$10^7$ PFU/ml (FIG. 12). This virus was additionally passaged 3 times on Vero cells (no increase in titers was detected) and then used for infecting mice.

Six-week-old NIH Swiss mice were immunized with 2 doses (4.6 and 5.6 log10 PFU) of the SIN/C$_{EEE\text{-}WEE}$/WEEV chimera and held for 4 weeks, then bled. Seropositivity rates were 8/10 (≥1:20 plaque reduction neutralization 80% titer) for the low dose and 5/5 for the high dose, with mean titers of 420 and 416, respectively (Table 3).

TABLE 3

Neutralizing antibody titers in female 10 week-old NIH Swiss mice 4 weeks after immunization with the SIN//EEE/WEEV chimera

| Vaccine dose ($\log_{10}$ PFU/mouse) | Mean 80% PRNT titer ± SD | No. seropositive |
|---|---|---|
| 4.6 | 420 ± 252 | 8/10 |
| 5.6 | 416 ± 215 | 5/5 |

All of the immunized mice continued to gain weight, with no difference compared to sham-vaccinated mice (FIG. 13).

Figure 15:
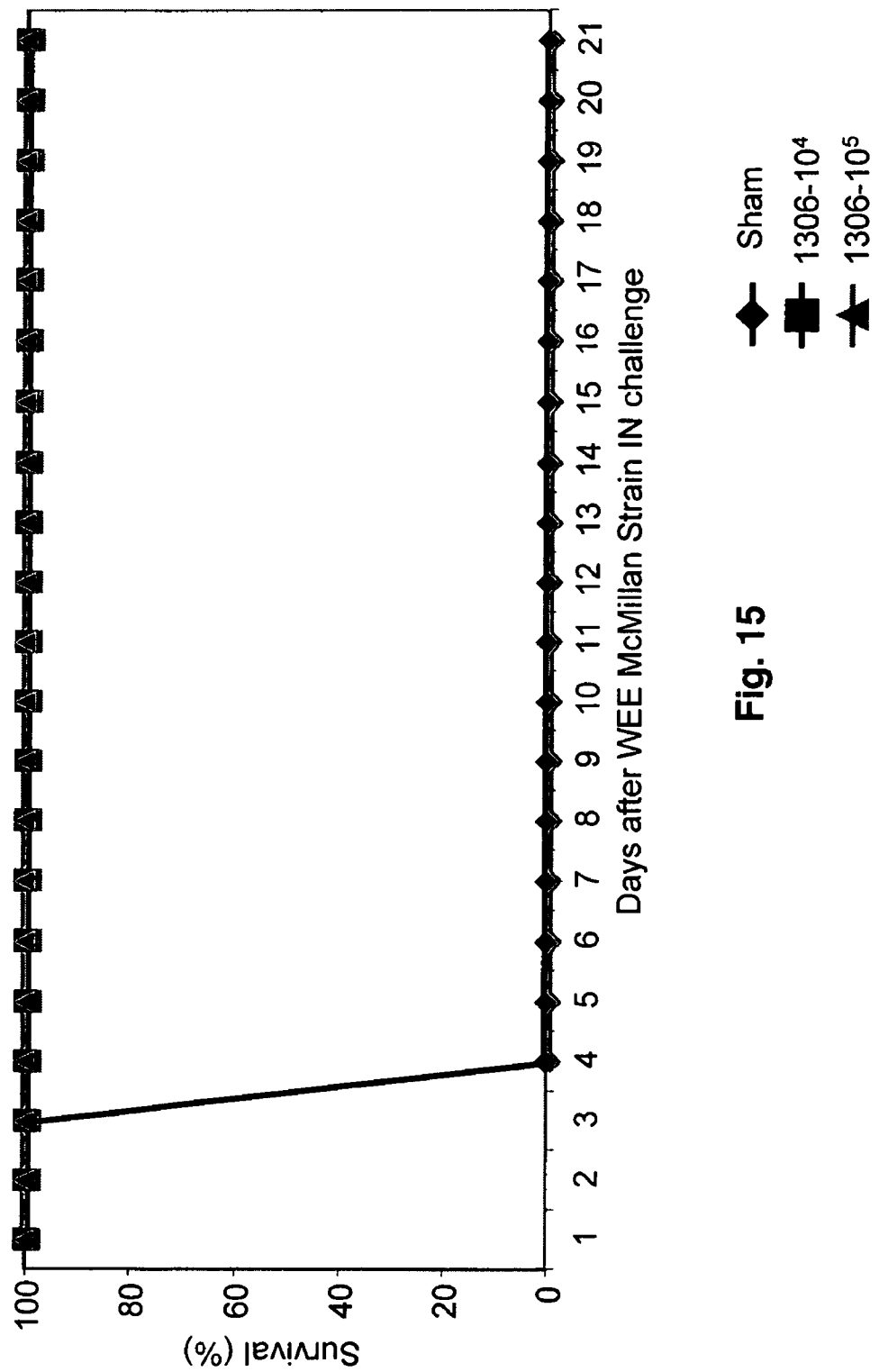
FIG. 15 shows mortality in 10-week old vaccinated or sham vaccinated mice after intranasal challenge ($10^5$ PFU) with the McMillan strain of WEEV or after sham vaccination.

Four weeks after vaccination, mice were challenged intranasally with $10^5$ PFU of the McMillan WEEV strain. Sham-vaccinated mice began losing weight by day 3 after challenge (FIG. 14), and all died by day 4 (FIG. 15). In contrast, all mice vaccinated with either dose survived and maintained or gained weight during the 3 weeks after challenge. These data demonstrate the attenuation, immunogenicity and efficacy of the SIN/C$_{EEE\text{-}WEE}$/WEEV chimeric vaccine candidate.

The following references were cited herein:

Beaty et al., Arboviruses, p 797-855. In N. J. Schmidt and R. W. Emmons (ed), Diagnostic procedures for viral, rickettsial and chlamydial infections, 6$^{th}$ edition. American Public Health Association, Washington, D.C.

McKnight et al., *J Virol,* 1996, 70: 1981-1989.

Paessler et al., *J Virol,* 2003, 77: 9278-9286.

Paessler et al., *J Virol,* 2006, 80: 2784-2796.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A chimeric alphavirus nucleic acid comprising a Sindbis virus genomic sequence having the Sindbis virus structural genes replaced with Western equine encephalitis virus (WEEV) structural genes, wherein the WEEV structural genes encode WEEV structural proteins comprising (i) a WEEV capsid protein having an Eastern equine encephalitis virus (EEEV) capsid protein RNA binding domain and (ii) WEEV glycoproteins.

2. The nucleic acid of claim 1, wherein the nucleic acid is RNA.

3. The nucleic acid of claim 1, wherein the WEEV is a C092-1356 strain or a McMillan strain of WEEV.

4. The nucleic acid of claim 1, wherein the EEEV capsid protein RNA binding domain is an EEEV Florida 93 strain capsid protein RNA binding domain.

5. A cell in culture expressing the nucleic acid of claim 1.

6. A chimeric alphavirus particle comprising the nucleic acid of claim 1.

7. A method of inducing an immune response in a subject comprising administering the chimeric alphavirus particle of claim 6.

* * * * *